United States Patent
Levijoki et al.

(10) Patent No.: US 10,092,510 B2
(45) Date of Patent: Oct. 9, 2018

(54) VETERINARY METHOD FOR INDUCING EMESIS

(71) Applicant: Orion Corporation, Espoo (FI)

(72) Inventors: Jouko Levijoki, Helsinki (FI); Lasse Saloranta, Sauvo (FI); Johanna Kokkonen, Espoo (FI)

(73) Assignee: ORION CORPORATION, Espoo (FI)

(*) Notice: Subject to any disclaimer, the term of this patent is extended or adjusted under 35 U.S.C. 154(b) by 0 days.

(21) Appl. No.: 15/025,681

(22) PCT Filed: Sep. 29, 2014

(86) PCT No.: PCT/FI2014/000022
§ 371 (c)(1),
(2) Date: Mar. 29, 2016

(87) PCT Pub. No.: WO2015/044504
PCT Pub. Date: Apr. 2, 2015

(65) Prior Publication Data
US 2016/0206555 A1 Jul. 21, 2016

Related U.S. Application Data

(60) Provisional application No. 61/884,924, filed on Sep. 30, 2013.

(51) Int. Cl.
| | | |
|---|---|---|
| *A61K 9/00* | (2006.01) | |
| *A61K 31/38* | (2006.01) | |
| *A61K 31/404* | (2006.01) | |
| *A61K 31/428* | (2006.01) | |
| *A61K 31/435* | (2006.01) | |
| *A61K 31/48* | (2006.01) | |
| *A61K 31/506* | (2006.01) | |
| *A61K 31/519* | (2006.01) | |
| *A61K 9/08* | (2006.01) | |
| *A61K 31/4045* | (2006.01) | |

(52) U.S. Cl.
CPC .............. *A61K 9/0048* (2013.01); *A61K 9/08* (2013.01); *A61K 31/38* (2013.01); *A61K 31/404* (2013.01); *A61K 31/4045* (2013.01); *A61K 31/428* (2013.01); *A61K 31/435* (2013.01); *A61K 31/48* (2013.01); *A61K 31/506* (2013.01); *A61K 31/519* (2013.01)

(58) Field of Classification Search
USPC .......................................... 514/411, 418, 323
See application file for complete search history.

(56) References Cited

FOREIGN PATENT DOCUMENTS

| FR | 2 661 832 A1 | 11/1991 | |
|---|---|---|---|
| WO | WO 2008/140052 A1 | 11/2008 | |
| WO | WO 2008140052 | * 11/2008 | ........... C07D 209/34 |

OTHER PUBLICATIONS

Darmani, N. A. et al.; "The Role of D2 and D3 Dopamine Receptors in the Mediation of Emesis in *Cryptotis parva* (The Least Shrew)"; J. Neural Transm.; vol. 106, Nos. 11-12; pp. 1045-1061; Feb. 15, 1999.

Horowski, R. et al.; "Direct Dopaminergic Action of Lisuride Hydrogen Maleate, an Ergot Derivative, in Mice"; European Journal of Pharmacology; vol. 36, No. 2; pp. 373-383; Apr. 1976.

Osinki, M. A. et al.; "Dopamine D2, but Not D4, Receptor Agonists Are Emetogenic in Ferrets"; Pharmacology Biochemistry and Behavior; vol. 81, No. 1; pp. 211-219; May 2005.

Ray, A. P. et al.; "Receptor-Selective Agonists Induce Emesis and Fos Expression in the Brain and Enteric Nervous System of the Least Shrew (*Cryptotis parva*)"; Pharmacology Biochemistry and Behavior; vol. 94, No. 1; pp. 211-218; Nov. 2009.

* cited by examiner

*Primary Examiner* — Pancham Bakshi
(74) *Attorney, Agent, or Firm* — Finnegan, Henderson, Farabow, Garrett & Dunner, L.L.P.

(57) ABSTRACT

The invention relates to a method of inducing emesis in animals, particularly companion animals such as dogs and cats, in situations where vomiting is desired. The method comprises administering an eye drop composition comprising a selective $D_2$ family dopamine agonist as an active ingredient to the eye of the animal to induce emesis. The method and the composition are useful in situations involving ingestion of a potentially toxic substance or foreign body by the animal.

4 Claims, No Drawings

VETERINARY METHOD FOR INDUCING EMESIS

This is a national stage application under § 371 of International Patent Application No. PCT/FI2014/000022, filed Sep. 29, 2014, which claims the benefit of U.S. Provisional Application No. 61/884,924, filed Sep. 30, 2013, both of which are incorporated herein by reference.

TECHNICAL FIELD

The present invention relates to a field of veterinary medicine. In particular, the invention relates to a method of inducing emesis in animals, particularly companion animals such as dogs and cats, in situations where vomiting is desired. Such situations include ingestion of a potentially toxic substance or foreign body by the animal. The method comprises administering an eye drop composition comprising a selective $D_2$ family dopamine agonist as an active ingredient to the eye of the animal to induce emesis.

BACKGROUND OF THE INVENTION

Emesis is a neurologically mediated reflex act that serves as a protective mechanism, helping to remove ingested toxic or noxious substances from the gastrointestinal (GI) tract. Vomiting can be caused by primary GI, renal, or hepatic diseases, central nervous system (CNS) disorders, electrolyte changes, pancreatitis, and metabolic problems or may be due to ingestion of noxious substances. When ingestion of potentially toxic substance or foreign body occurs in companion animals such as dogs or cats, induction of emesis is often the first line of action. Intoxication as a result of oral exposure of poisonous chemicals, plants or human food (e.g. chocolate) is potentially a life threatening situation in dogs. Timely decontamination through use of emetics, serves in most cases to reduce systemic absorption acutely after exposure. Removing foreign body through emesis saves the dogs in many cases from endoscopic or surgical intervention.

Table salt is commonly used by owners even though it does not always induce emesis. Furthermore, large doses of table salt can cause serious hypernatremia. Orally administered hydrogen peroxide induces emesis in many dogs. Potential side effects of hydrogen peroxide are irritation of gastrointestinal tract, haemorrhagic gastritis, gastric dilatation volvulus and aspiration pneumonia. Historically also mustard powder, soap and syrup of ipecac have been recommended for use as an emetic agent, but are no longer standard of care due to side effects and lack of efficacy. Subcutaneously administered apomorphine has been used for induction of emesis in dogs. However, apomorphine has a disadvantage that it also exhibits anti-emetic effect mediated by opioid μ receptors in the vomiting centre in the brain. The side effects of apomorphine include prolonged vomiting, excitation, depression and local irritation. Apomorphine is contraindicated with medications that can result in respiratory or central nervous system depression. None of the existing approaches to induce emesis works reliably, and many have undesirable side effects. Further, no veterinary-labelled product is available that could be easily and safely administered by the animal owner at home.

SUMMARY OF THE INVENTION

It has been found that emesis can be induced in animals, particularly companion animals such as dogs and cats, by administering an eye drop composition comprising a selective $D_2$ family dopamine agonist to the eye of the animal. The method produces rapid and consistent onset of action in animals without inducing more prolonged vomiting than necessary. Moreover, the method has been found to be safe, free of adverse effects and devoid of ocular discomfort. As the composition can be easily administered by the pet owner at home in acute situations, the present invention provides a significant improvement in the treatment of acute intoxication of animals, particularly companion animals such as dogs and cats.

Thus, according to one embodiment of the invention, the present invention provides a method for inducing emesis in animals, particularly dogs and cats, the method comprising administering an effective amount of an eye drop composition comprising a selective $D_2$ family dopamine agonist as an active ingredient to the eye of the animal in need thereof.

According to another embodiment of the invention, the present invention provides an eye drop composition comprising a selective $D_2$ family dopamine agonist as an active ingredient for use in inducing emesis in animals, particularly dogs and cats.

According to another embodiment of the invention, the present invention provides the use of an eye drop composition comprising a selective $D_2$ family dopamine agonist as an active ingredient in the manufacture of a medicament for inducing emesis in animals, particularly dogs and cats.

According to one embodiment of the invention the animal to be treated is a dog.

According to still another embodiment of the invention, the present invention provides an eye drop composition comprising 0.2-5%, per weight of the composition, of a selective $D_2$ family dopamine agonist, and 90-99.8% of sterile water.

According to one embodiment of the invention, the present invention provides a veterinary kit comprising a) a composition comprising 0.2-5%, per weight of the composition, of a selective $D_2$ family dopamine agonist, and 90-99.8% of sterile water, b) a package for containing said composition, and c) instructions for administering said composition on the eye of an animal, particularly a dog or cat, for inducing emesis.

DETAILED DESCRIPTION OF THE INVENTION

The term "emesis", as used herein, refers to vomiting (the actual expulsion of stomach contents), retching (vomiting movements without expulsion of matter) and the concomitant nausea associated with such conditions.

The term "a selective $D_2$ family dopamine agonist", as used herein, refers to an agonist which binds to a $D_2$ type receptor subfamily member (a $D_2$, $D_3$ or $D_4$ receptor) with a higher affinity than to a $D_1$ type receptor subfamily member (a $D_1$ or $D_5$ receptor) and which is more selective for a $D_2$ type receptor subfamily member over opioid μ receptor than apomorphine. Examples of selective $D_2$ family dopamine agonists include, but are not limited to, ropinirole, pramipexole, sumanirole, lisuride, quinagolide, rotigotine, bromocriptine, cabergoline, pergolide, piribedil and pharmaceutically acceptable salts thereof.

The term "administration to the eye", as used herein, refers to applying topically to the eye and surrounding tissues, particularly to the inner surface of the eye and the inner surface of the eyelids (including e.g. cornea, conjunctiva and sclera). The term includes, for example, instillation administration, administration into conjunctival sac and conjunctival administration.

The term "eye drop composition", as used herein, refers to a liquid or semisolid pharmaceutical composition adapted to administration to the eye. Typical example of an eye drop composition is an ophthalmic solution to be administered dropwise to the eye.

The present invention relates to a method for inducing emesis in animals, particularly dogs, the method comprising administering an effective amount of an eye drop composition comprising a selective $D_2$ family dopamine agonist as an active ingredient to the eye of the animal in need thereof. Examples of selective $D_2$ family dopamine agonists include, but are not limited to, ropinirole, pramipexole, sumanirole, lisuride, quinagolide, rotigotine, bromocriptine, cabergoline, pergolide, piribedil and pharmaceutically acceptable salts thereof.

According to one embodiment, the selective $D_2$ family dopamine agonist is selected from ropinirole, pramipexole, sumanirole, lisuride, quinagolide, rotigotine, bromocriptine, cabergoline, pergolide, piribedil and pharmaceutically acceptable salts thereof.

According to another embodiment of the invention, the selective $D_2$ family dopamine agonist is selected from ropinirole, pramipexole, sumanirole, lisuride, quinagolide, rotigotine, and pharmaceutically acceptable salts thereof.

According to another embodiment of the invention, the selective $D_2$ family dopamine agonist is selected from ropinirole, pramipexole, sumanirole, lisuride and pharmaceutically acceptable salts thereof.

According to still another embodiment of the invention, the selective $D_2$ family dopamine agonist is selected from ropinirole, pramipexole and pharmaceutically acceptable salts thereof.

The amount of the active ingredient to be administered is suitably selected such as to provide sufficient emetic effect. Accordingly, for inducing emesis in companion animals such as dogs and cats, a selective $D_2$ family dopamine agonist or a pharmaceutically acceptable salt thereof is administered to the eye in an amount of 5 to 1000 µg/kg, more typically from 10 to 600 µg/kg.

For example, ropinirole or a pharmaceutically acceptable salt thereof, preferably hydrochloride salt, is suitably administered to the eye of the companion animals such as dogs or cats in an amount of 20-450 µg/kg, particularly 50-300 µg/kg. Pramipexole or a pharmaceutically acceptable salt thereof, preferably dihydrochloride salt, is suitably administered to the eye of the companion animals such as dogs and cats in an amount of 10-200 µg/kg, particularly 20-100 µg/kg.

The actual amount of the drug to be administered may depend on numerous factors, such as the species, age and weight of the subject to be treated, the active ingredient used, and the type of the composition.

The selective $D_2$ family dopamine agonist can be formulated into a dosage form adapted for administration to the eye by combining the drug substance with conventional pharmaceutical diluents and carriers commonly used in eye drop compositions. The eye drop composition useful in the method of the invention may be, for example, in a liquid or semisolid form such as in the form of a solution, emulsion or suspension.

Preferably, the eye drop composition is in the form of a aqueous solution adapted for administration to the eye of the animal. The concentration of a selective $D_2$ family dopamine agonist in the eye drop composition, e.g. in the aqueous solution composition, is typically within the range of about 0.01 to about 20% (w/w), more typically from about 0.1 to about 15% (w/w), for example from about 0.2 to about 10% (w/w), per weight of the composition, depending on the drug substance used.

For example, the concentration of ropinirole or a pharmaceutically acceptable salt thereof, for example hydrochloride salt, in the eye drop composition, e.g. aqueous solution composition, is typically within the range of about 0.1 to about 15% (w/w), more typically from about 0.2 to about 10% (w/w), still more typically from 0.3 to 8% (w/w), for example from 0.5 to 6% (w/w), per weight of the composition. The concentration of pramipexole or a pharmaceutically acceptable salt thereof, for example dihydrochloride salt, in the eye drop composition, e.g. aqueous solution composition, is typically within the range of about 0.05 to about 10% (w/w), more typically from about 0.1 to about 6% (w/w), still more typically from about 0.15 to 5% (w/w), for example from 0.2 to 3% (w/w), per weight of the composition.

According to one embodiment, the eye drop composition comprises 0.2-10%, per weight of the composition, of a selective $D_2$ family dopamine agonist, and 90-99.8% of sterile water. The composition may additionally comprise a tonicity agent such as sodium chloride, pH adjusting agents or buffering agents such as sodium hydroxide, hydrochloric acid, citric acid/sodium citrate, tartaric acid, fumaric acid, antioxidants such as butylated hydroxyanisole (BHA) or butylated hydroxytoluene (BHT), chelating agents such as edetate disodium, thickening agents such as sodium carboxymethylcellulose and other ingredients commonly used in the preparation of eye drop compositions.

The pH of the eye drop composition is within the range of from about 3 to about 11, depending on the drug substance used. For example, the pH of the eye drop composition comprising ropinirole or a pharmaceutically acceptable salt thereof, for example hydrochloride salt, is suitably within the range of from about 2.5 to about 8, preferably from 3 to about 6, for example from about 3.5 to about 5. The pH of the eye drop composition comprising pramipexole or a pharmaceutically acceptable salt thereof, for example dihydrochloride salt, is suitably within the range of from about 8 to about 11, preferably from about 8.5 to about 10.5, for example from about 9 to about 10.

The eye drop composition is preferably given to the eye of the animal from a prefilled bottle, ampoule or pipette in a volume ranging typically from about 0.01 to about 0.3 ml, more preferably from about 0.015 to about 0.2 ml, for example from 0.02 to 0.15 ml, of the eye drop composition. The administration can be repeated if no vomiting occurs within 15 minutes.

The composition can be provided in the form of a veterinary kit that comprises the eye drop composition, a package for containing said composition, and instructions for administering said composition to the eye of an animal, particularly a companion animal such as dog, for inducing emesis. Preferably, said package is an applicator, e.g. a squeezable prefilled single-use bottle, ampoule or pipette capable of dosing fixed volumes of the composition of the invention. The squeezable bottle, ampoule or pipette is preferably prepared form polymer material, such as LDPE. Suitably, the volume of the suitable bottle, ampoule or pipette ranges from about 0.5 to 5 ml. For example, about 0.5 to about 2 ml of the eye drop composition can be filled into single use blow fill seal (BFS) LDPE ampoules having volume of 0.5 ml, 1 ml or 2 ml.

In situations where vomiting of the animal is desired, suitable amount of the eye drop composition comprising a selective $D_2$ family dopamine agonist is administered to one or both eyes of the animal. The vomiting starts within 15 minutes, more typically within about 10 minutes, still more typically within about 6 minutes, from the administration. The vomiting ends within 60 minutes, more typically within about 30 minutes. When ropinirole or a pharmaceutically acceptable salt thereof is used in the eye drop composition, the vomiting ends typically within about 20 minutes from the administration.

Ropinirole, pramipexole and pharmaceutically acceptable salts thereof have been found to provide particularly consistent and rapid onset of emesis without producing unnecessarily prolonged emesis, ocular discomfort or significant local irritation when administered to the eye of the animal. Ropinirole or a pharmaceutically acceptable salt thereof is particularly preferred for use as an active ingredient in the eye drop composition for inducing emesis in animals, particularly companion animals such as dogs or cats.

The invention is further illustrated by the following examples, which are not meant to limit the scope of the invention.

FORMULATION EXAMPLE 1

| | |
|---|---|
| Ropinirole hydrochloride | 11.4 mg (equivalent to 10 mg of ropinirole base) |
| Hydrochloric acid | to adjust to pH 4 |
| Sodium chloride | to adjust osmolality (300-400 mosm/kg) |
| Water for injection | ad 1 ml |

FORMULATION EXAMPLE 2

| | |
|---|---|
| Ropinirole hydrochloride | 45.6 mg (equivalent to 40 mg of ropinirole base) |
| Sodium chloride | to adjust osmolality (300-400 mosm/kg) |
| Water for injection | ad 1 ml |
| | pH 4 |

FORMULATION EXAMPLE 3

| | |
|---|---|
| Pramipexole dihydrochloride monohydrate | 7.15 mg (equivalent to 5 mg of pramipexole base) |
| Sodium hydroxide | to adjust to pH 10 |
| Sodium chloride 0.9% solution | ad 1 ml |

FORMULATION EXAMPLE 4

| | |
|---|---|
| Ropinirole hydrochloride | 34.2 mg (equivalent to 30 mg of ropinirole base) |
| Citric acid monohydrate | 2.5 mg |
| Sodium citrate | 2.1 mg |
| Sodium chloride | to adjust osmolality (300-400 mosm/kg) |
| Hydrochloric acid/Sodium hydroxide | if needed to adjust to pH 4 |
| Water for injection | ad 1 ml |

FORMULATION EXAMPLE 5

| | |
|---|---|
| Ropinirole hydrochloride | 57 mg (equivalent to 50 mg of ropinirole base) |
| Citric acid monohydrate | 2.5 mg |
| Sodium citrate | 2.1 mg |
| Sodium chloride | to adjust osmolality (300-400 mosm/kg) |
| Hydrochloric acid/Sodium hydroxide | if needed to adjust to pH 4 |
| Water for injection | ad 1 ml |

FORMULATION EXAMPLE 6

| | |
|---|---|
| Pramipexole dihydrochloride monohydrate | 2.86 mg (equivalent to 2 mg of pramipexole base) |
| Diethanolamine | 8 mg |
| Edetate disodium | 1.1 mg |
| Sodium carboxymethylcellulose | 5 mg |
| Sodium chloride | to adjust osmolality (300-400 mosm/kg) |
| Hydrochloric acid/Sodium hydroxide | if needed to adjust to pH 9 |
| Water for injection | ad 1 ml |

FORMULATION EXAMPLE 7

| | |
|---|---|
| Pramipexole dihydrochloride monohydrate | 2.86 mg (equivalent to 2 mg of pramipexole base) |
| Sodium bicarbonate | 4 mg |
| Edetate disodium | 1.1 mg |
| Sodium carboxymethylcellulose | 5 mg |
| Sodium chloride | to adjust osmolality (300-400 mosm/kg) |
| Hydrochloric acid/Sodium hydroxide | if needed to adjust to pH 10 |
| Water for injection | ad 1 ml |

FORMULATION EXAMPLE 8

| | |
|---|---|
| Pramipexole dihydrochloride monohydrate | 7.15 mg (equivalent to 5 mg of pramipexole base) |
| Diethanolamine | 8 mg |
| Edetate disodium | 1.1 mg |
| Sodium carboxymethylcellulose | 5 mg |
| Sodium chloride | to adjust osmolality (300-400 mosm/kg) |
| Hydrochloric acid/Sodium hydroxide | if needed to adjust to pH 10 |
| Water for injection | ad 1 ml |

FORMULATION EXAMPLE 9

| | |
|---|---|
| Ropinirole hydrochloride | 57 mg (equivalent to 50 mg of ropinirole base) |
| Tartaric acid | 10 mg |
| Edetate disodium | 1.1 mg |
| Sodium carboxymethylcellulose | 5 mg |
| Hydrochloric acid/Sodium hydroxide | if needed to adjust to pH 4 |
| Water for injection | ad 1 ml |

FORMULATION EXAMPLE 10

| | |
|---|---|
| Ropinirole hydrochloride | 57 mg (equivalent to 50 mg of ropinirole base) |
| Tartaric acid | 10 mg |
| Edetate disodium | 1.1 mg |
| Sodium carboxymethylcellulose | 5 mg |
| BHT | 0.1 mg |
| BHA | 0.1 mg |
| Hydrochloric acid/Sodium hydroxide | if needed to adjust to pH 4 |
| Water for injection | ad 1 ml |

FORMULATION EXAMPLE 11

| | |
|---|---|
| Ropinirole hydrochloride | 57 mg (equivalent to 50 mg of ropinirole base) |
| Fumaric acid | 10 mg |
| Edetate disodium | 1.1 mg |
| Sodium carboxymethylcellulose | 5 mg |
| Hydrochloric acid/Sodium hydroxide | if needed to adjust to pH 4 |
| Water for injection | ad 1 ml |

FORMULATION EXAMPLE 12

| | |
|---|---|
| Ropinirole hydrochloride | 57 mg (equivalent to 50 mg of ropinirole base) |
| Fumaric acid | 10 mg |
| Edetate disodium | 1.1 mg |
| Sodium carboxymethylcellulose | 5 mg |
| BHT | 0.1 mg |
| BHA | 0.1 mg |
| Hydrochloric acid/Sodium hydroxide | if needed to adjust to pH 4 |
| Water for injection | ad 1 ml |

The above formulations can be prepared by dissolving the excipients and drug substance in the carrier solution followed by sterilized filtration.

Experiment 1. Induction of emesis in dogs by eye drop solution of ropinirole

Aqueous eye drop solution comprising ropinirole hydrochloride (10 mg/ml or 40 mg/ml, pH 4) was administered into the eyes of six test dogs with doses of 50 µg/kg and 100 µg/kg for induction of emesis. The results are shown in Tables 1 and 2. The average induction time for emesis was 6.7 min with smaller dose and 4.8 min with higher dose. Vomiting ended on the average at 20.5 min with the smaller dose (fasted animals) and at 12.3 min with higher dose (fed animals). No prolonged emesis or significant irritation was seen with tested doses.

TABLE 1

Ropinirole HCl, pH 4, conc. 10 mg/ml, dose 50 µg/kg, both eyes, fasted

| Individual | Onset of the first vomit | The last vomit | Number of vomits |
|---|---|---|---|
| Dog 1 | 6 min | 20 min | 3 |
| Dog 2 | 11 min | 12 min | 2 |
| Dog 3 | 6 min | 36 min | 7 |
| Dog 4 | 7 min | 21 min | 3 |
| Dog 5 | 6 min | 20 min | 3 |
| Dog 6 | 4 min | 14 min | 3 |
| Average 6/6 | 6.7 | 20.5 | 3.5 |

TABLE 2

Ropinirole HCl, pH 4, conc. 40 mg/ml, dose 100 µg/kg, right eye, fed

| Individual | Onset of the first vomit | The last vomit | Number of vomits |
|---|---|---|---|
| Dog 1 | 5 min | 15 min | 2 |
| Dog 2 | 6 min | 20 min | 4 |
| Dog 3 | 3 min | 20 min | 3 |
| Dog 4 | 6 min | 9 min | 2 |
| Dog 5 | 2 min | 10 min | 2 |
| Dog 6 | 7 min | 7 min | 1 |
| Average 6/6 | 4.8 | 12.3 | 2.3 |

Experiment 2. Induction of emesis in dogs by eye drop solution of pramipexole

Aqueous eye drop solution comprising pramipexole (5 mg/ml, pH 10) was administered into the eyes of six test dogs with dose of 30 µg/kg for induction of emesis. The results are shown in Table 3. The average induction time for emesis was 4.5 min. Vomiting ended on the average at 31.3 min. No prolonged emesis or significant irritation was seen with tested dose.

TABLE 3

Pramipexole, pH 10, conc. 5 mg/ml, dose 30 µg/kg, both eyes

| Individual | Onset of the first vomit | The last vomit | Number of vomits |
|---|---|---|---|
| Dog 1 | 4 min | 27 min | 3 |
| Dog 2 | 3 min | 22 min | 3 |
| Dog 3 | 3 min | 62 min | 6 |
| Dog 4 | 12 min | 12 min | 1 |
| Dog 5 | 2 min | 62 min | 6 |
| Dog 6 | 3 min | 3 min | 1 |
| Average 6/6 | 4.5 | 31.3 | 3.3 |

The invention claimed is:

1. A method for inducing emesis in a dog in situations involving ingestion of a potentially toxic foreign substance or foreign body, comprising administering to the eye of the dog in need thereof an effective amount of a composition comprising ropinirole or a pharmaceutically acceptable salt thereof, and wherein emesis thereafter occurs.

2. The method according to claim 1, wherein ropinirole or a pharmaceutically acceptable salt thereof is administered in an amount of 20 µg/kg to 450 µg/kg.

3. The method according to claim 2, wherein ropinirole or a pharmaceutically acceptable salt thereof is administered in an amount of 50 µg/kg to 300 µg/kg.

4. The method according to claim 1, wherein the composition is in the form of an eye drop.

* * * * *